(12) United States Patent
Wang et al.

(10) Patent No.: US 8,747,469 B2
(45) Date of Patent: Jun. 10, 2014

(54) GRAFT FIXATION DEVICE

(75) Inventors: Bin Wang, Aberdeen (GB); Chizari Mahmoud, London (GB); David Martyn Snow, Manchester (GB)

(73) Assignee: University Hospital of South Manchester NHS Foundation Trust, Manchester (GB)

( * ) Notice: Subject to any disclaimer, the term of this patent is extended or adjusted under 35 U.S.C. 154(b) by 488 days.

(21) Appl. No.: 12/601,181

(22) PCT Filed: May 27, 2008

(86) PCT No.: PCT/GB2008/001800
§ 371 (c)(1),
(2), (4) Date: Nov. 20, 2009

(87) PCT Pub. No.: WO2008/145984
PCT Pub. Date: Dec. 4, 2008

(65) Prior Publication Data
US 2010/0174369 A1 Jul. 8, 2010

(30) Foreign Application Priority Data

May 25, 2007 (GB) .................................. 0710023.3

(51) Int. Cl.
*A61F 2/08* (2006.01)

(52) U.S. Cl.
USPC ...................................... 623/13.14; 623/13.15

(58) Field of Classification Search
USPC ............ 623/13.14, 13.15; 606/300, 313, 327; 411/21, 38
See application file for complete search history.

(56) References Cited

U.S. PATENT DOCUMENTS 5,176,682 A 1/1993 Chow
7,828,802 B2 * 11/2010 Levy et al. ...................... 606/63
2010/0161055 A1 * 6/2010 Donnelly et al. .......... 623/13.14

FOREIGN PATENT DOCUMENTS

EP 1 297 799 A2 4/2003
EP 1 905 385 A 4/2008
FR 2 622 430 A1 5/1989
WO WO-2005/051205 A1 6/2005

* cited by examiner

*Primary Examiner* — Bruce E Snow
(74) *Attorney, Agent, or Firm* — Dickstein Shapiro LLP

(57) ABSTRACT

A graft fixation device (1) comprising a sheath (2) having a body (9) that defines an inner longitudinal bore (8) and a member (3) for receipt within said bore (8), wherein said sheath (2) comprises at least one projection (15) moveably connected to said sheath body (9) and said at least one projection (15) is arranged so as to be displaceable radially outwardly of said sheath body (9) upon receipt of said member (3) within said bore (8).

12 Claims, 7 Drawing Sheets

GRAFT FIXATION DEVICE

The present invention relates to a graft fixation device comprising a sheath having a body that defines an inner longitudinal bore and a member for receipt within said bore. The device may be used to fix any form of graft, for example a soft tissue graft, such as a graft ligament or tendon, to a support structure, such as a joint with a pre-formed bone tunnel.

Damage to connective soft tissue, for example ligaments and tendons, often results from excessive and/or uncontrolled motion about a particular joint, such as the knee or elbow. In severe cases, surgery can be required to restore the joint's function by replacement or reconstruction of the damaged connective soft tissue, often using graft tissue. During such procedures the graft tissue will usually have to be secured or fixed to an appropriate support structure, such as one or more of the bones forming part of the joint in question.

The anterior cruciate ligament (ACL), which runs from the front of the tibia to the back of the femur, helps to stabilize the knee by preventing the tibia from moving too far forward. The demands placed on the knee sometimes exceed its limits and if the ligament is stretched too tightly, it can tear or rupture. By way of example, ACL injuries may occur when the upper leg is turned outward while the lower leg is turning inward. This type of injury most commonly happens to athletes when quickly pivoting or changing direction.

If the ACL is severely damaged it can be surgically repaired to restore the knee's stability and function. Approximately 100,000 ACL reconstructions are performed in the US each year, and the numbers are rising.[1] A widely used ACL repair procedure is the bone-tendon-bone patella tendon repair procedure, although there is a growing trend for the use of soft tissue grafts, e.g. replacing the torn ACL with a hamstring tendon graft harvested from the patient.

In spite of surgical advances, the failure rate of ACL reconstruction is quoted to be in the range of 5 to 25%,[2] with the main cause of graft failure being loss of graft fixation within the tibial bone tunnel. Most current ACL repair procedures employ traditional interference screws to press a graft against a tibial and/or femoral bone tunnel wall. A disadvantage of using such screws is the screw thread which provides the fixation within the bony tunnel. The larger and sharper the thread the better the fixation, but conversely the greater the damage caused to the tendon and therefore the risk of failure.

The pull-out strength of current fixation screws is markedly reduced in circumstances where the support structure possesses reduced bone mineral density. Accordingly, ACL reconstruction in middle-aged individuals is rarely performed, especially in peri-menopausal women. Moreover, as ACL reconstruction is increasingly being performed on a more active older population with reduced bone quality, the ACL reconstruction failure rate is set to increase still further unless improved forms of fixation are developed.

An object of the present invention is to obviate or mitigate one or more of the above problems and/or disadvantages. A further object is to provide an improved device for graft fixation.

According to a first aspect of the present invention there is provided a graft fixation device comprising a sheath having a body that defines an inner longitudinal bore and a member for receipt within said bore, wherein said sheath comprises at least one projection moveably connected to said sheath body and said at least one projection is arranged so as to be displaceable radially outwardly of said sheath body upon receipt of said member within said bore.

By way of example only, the device can be used to fix a graft to a support structure, such as a bone tunnel, by placing the sheath into the tunnel between strands of the graft and then inserting the member into the bore of the sheath body. This causes outwards radial displacement of the projections relative to the sheath body so that they contact and compress the graft against the tunnel wall creating strong, rigid fixation.

A second aspect of the present invention provides use of a device according to the first aspect of the present invention to fix a graft to a support structure.

The present invention provides a superior means of graft fixation than those currently available and removes any need for secondary fixation. Computer modelling using finite element analysis indicates that the device of the first aspect of the present invention will impart significantly greater pressure on a graft against a support structure (e.g. a bony tunnel) than conventional methods of fixation. Moreover, the modelling also predicts that the device of the first aspect of the present invention will fix a graft to a support structure, such as a tibial bone tunnel, such that the force required to pull the graft from the support structure will be up to around 180% greater than the force required if a traditional interference screw is used. Proof of principle tests have demonstrated that even a rudimentary prototype device according to the first aspect of the present invention performs similarly to a commercially available device. Further development of the device in terms of materials, and the size, shape and structure of detailed features should provide a range of different devices according to the first aspect of the present invention which are optimised for different applications and outperform current commercially available devices. The device of the first aspect of the present invention should therefore allow more aggressive rehabilitation in the young and enable connective soft tissue reconstruction in an increasingly active older population, which is currently excluded over worries regarding inferior bone quality.

The device of the first aspect of the present invention is eminently suitable for use in the fixation of anterior cruciate graft ligaments.

A third aspect of the present invention provides an anterior cruciate graft ligament fixation device comprising a sheath having a body that defines an inner longitudinal bore and a member for receipt within said bore, wherein said sheath comprises at least one projection moveably connected to said sheath body and said at least one projection is arranged so as to be displaceable radially outwardly of said sheath body upon receipt of said member within said bore.

A fourth aspect of the present invention provides use of a device according to the third aspect of the present invention to fix an anterior cruciate graft ligament to a surface of bone within a tibial bone tunnel.

A fifth aspect of the present invention provides a method for fixing a graft to a support structure using a device comprising a sheath having a body that defines an inner longitudinal bore and a member for receipt within said bore, said sheath comprising at least one projection that is moveably connected to said sheath body, wherein the method comprises placing the sheath adjacent the graft and the support structure and inserting the member into the bore of the sheath body so as to displace said at least one projection radially outwardly of said sheath body so that said at least one projection contacts the graft and urges it against the support structure.

The device of the present invention comprises at least one projection that is moveably connected to the sheath body, that is, the or each projection is arranged such that it is moveable relative to the sheath body rather than being fixed to the sheath body in such a manner that it/they can only move in unison with the sheath body. This latter situation is the case with some conventional fixation systems which employ expansion screws inserted into expandable sheaths carrying fixed external projections (as modelled in Comparative Example 2 below).

The means of connection between the or each projection and the sheath body may be arranged to provide any desirable type of relative movement. It is preferred that said at least one projection is pivotally or hingedly connected to said sheath body.

Preferably said sheath body defines a distal end wall and an opposite proximal end wall, said distal and proximal end walls being connected by a side wall. While the sheath body may take any suitable form, it is preferred that the sheath body is hollow and the side wall is preferably continuous and most preferably defines an annular cross-section. The side wall is preferably tapered radially inwardly from said proximal end wall to said distal end wall. The side wall may have any appropriate taper angle but a taper angle of up to around 5° is preferred. More preferably the taper angle is around 2° to around 5°, yet more preferably around 3° to around 4°, and most preferably around 3.7° to 3.9°. The sheath body preferably possesses a consistent taper along the entire length of its side wall, starting from a diameter of about 9 mm at its proximal end and reducing to about 7 mm at its distal end. The gradient along the sheath body is equivalent to a taper angle of about 3.88° along the body ($\tan^{-1} 2/30$).

The proximal end wall of the sheath body preferably defines a proximal opening to permit insertion of said member into the bore of said sheath body. The proximal end wall opening may take any size and shape provided it is appropriately dimensioned to permit insertion of the member through the opening and into the bore. Preferably the opening is substantially circular to facilitate easy and convenient insertion of the member.

The distal end wall of the sheath body may take any appropriate configuration and may be squared off, tapered or rounded. Preferably the distal end wall of the sheath body is tapered or rounded to aid implantation of the sheath body at the appropriate location for fixation of a graft. Most preferably the distal end wall is rounded to ease implantation and limit any damage which the distal end wall of sheath body may cause during implantation. It is preferred that the distal end wall defines a distal opening. The distal opening may be provided at any location in the distal end wall and may be of any suitable size and shape, although in a preferred embodiment, the distal end wall defines a central circular opening. The distal end wall of the sheath body may also define one or more, preferably four equiangularly spaced, longitudinal slots.

In a preferred embodiment of the first aspect of the present invention the or each projection is outwardly radially displaceable through an aperture defined by the side wall of the sheath body. The or each aperture may take any convenient size and shape provided it is of suitable configuration to enable the projection associated with that aperture to pass therethrough. The or each aperture may be circular, oval, square or of any other appropriate shape when viewed from the exterior of the sheath. In a preferred embodiment the or each aperture is substantially rectangular.

Preferably the or each projection is biased to at least partially project radially outwardly of the sheath body prior to receipt of said member within said bore. In this configuration it may be necessary to temporarily urge the or each projection radially inwardly so that it does not project radially outwardly of the sheath body during implantation of the sheath. The or each projection may be held temporarily in the inwardly directed position by use of a suitable implantation tool or the shape of a leading surface of each projection may be configured (e.g. tapered or rounded) such that during insertion said leading surface contacts a surface of the support structure (e.g. the bone tunnel) and in doing so urges the or each projection towards the inside of the sheath body.

Alternatively, the or each projection may be biased radially inwardly of the sheath body so as not to project radially outwardly of the sheath body prior to receipt of said member within said bore. In this way, the or each projection is already retained within the sheath body so as not to hinder insertion of the sheath into the implantation site.

Preferably the or each projection comprises a graft engaging portion, which may, for example, be in the form of one or more spikes or the like, and a connecting portion which connects the graft engaging portion to the sheath body. The connecting portion preferably comprises a distal end connected to the graft engaging portion and an opposite proximal end connected to said sheath body. The means of connection between the proximal end of the connecting portion and the sheath body may take any suitable form, but it is preferred that the proximal end of the connecting portion is pivotally or hingedly connected to said sheath body. The or each projection is preferably connected to the sheath body at or near to an edge of the aperture in the sheath body associated with that projection.

The or each projection may be formed separately to the sheath body or may be integrally formed with the sheath body. Where the or each projection is integrally formed with the sheath body, it is preferred that the or each projection is connected to the sheath body via a living hinge or pivot. More specifically, it is preferred that a living hinge or pivot connects the proximal end of the connecting portion of the or each projection to the sheath body.

It is preferred that the connecting portion of the or each projection comprises a surface facing towards said proximal opening of the sheath body, said surface being arranged so as to be contactable by said member upon insertion of the member into said bore. In this way, as the member is inserted through the proximal opening into the bore of the sheath body the member contacts said surface of the connecting portion of the or each projection which thereby urges that projection radially outwardly of the sheath body. The graft engaging portion and said connecting portion of the or each projection may be formed separately or may be integrally formed.

The device may incorporate any desirable number of projections, provided at any convenient location on the sheath. It will be appreciated that the particular number and arrangement of projections should be chosen to suit the specific intended application of the device. It may be sufficient to employ a device comprising a single projection. Alternatively, where the graft to be fixed comprises two strands it may be advantageous to employ a device with at least two angularly spaced (preferably diametrically opposed) projections so that one projection can contact and fix one of the two strands of the graft. Thus, the device preferably comprises at least two projections provided at positions that are angularly spaced about said sheath. Where grafts having more than two strands are to be fixed it may clearly be desirable to use a device comprising more than two angularly spaced projections. For example, in the Example set out below a hamstring tendon graft is used in an ACL reconstruction procedure and the graft comprises four strands to be fixed. In this example, and in other procedures where it is desired to fix four or more strands it is preferred that the device comprises four projections provided at positions that are equiangularly spaced about the sheath. It will, of course, be appreciated that a device comprising two or more (e.g. four) projections may be used to fix a graft having any number of strands, i.e. one, two, three or more. While it may be advantageous, it is not absolutely necessary to select a device having exactly the same number of angularly spaced projections as there are graft strands to be fixed. For commercial reasons it is likely to be most efficient to produce a range of standardised devices which are suitable for a range of applications. In this regard, it is particularly desirable that the device of the first aspect of the present invention comprises four equiangularly spaced projections.

Additionally or alternatively, the device may be provided with projections which are spaced longitudinally along the sheath to further improve the device's fixation properties. It is preferred that the device comprises at least two projections provided at positions that are longitudinally spaced along said sheath. In a preferred embodiment the device comprises three projections provided at positions that are equally longitudinally spaced along the sheath. In further preferred embodiments, the device may comprise three, four, five or more projections, some or all of which may be equally spaced from one another.

In a preferred embodiment the or each projection is outwardly radially displaceable by up to around 6 mm relative to the outer surface of the sheath body. More preferably the or each projection is outwardly radially displaceable by up to around 4 mm and most preferably by up to around 2 mm. In preferred embodiments where the device of the present invention incorporates diametrically opposite projections, it will be appreciated that if each projection can displace radially outwardly by up to around, for example, 2 mm, then the overall diameter of the device will increase by up to around 4 mm due to radial displacement of the spikes.

The sheath body may be formed of any appropriate material bestowing the body with any desirable characteristic. It is preferred that the sheath body is deformable radially outwardly upon receipt of said member within said bore. The degree to which the sheath body is deformable or expandable may be chosen to suit a particular application. Thus, in some applications it may be desirable to use a sheath body formed from a more flexible material which will facilitate greater radial deformation, whereas in some other applications it may be advantageous to employ a sheath body formed from a less flexible material which will exhibit lower radial deformation.

Additionally or alternatively, outward radial expansion of the sheath body upon insertion of the member may also be facilitated by the provision of suitable slots, apertures, openings, channels or the like defined by the sheath body. The aperture(s) defined by the side wall of the sheath body associated with the projection(s) may be configured to facilitate outward radial deformation or expansion of the sheath body upon insertion of the member into the bore of the sheath. Said expansion may arise, at least in part, due to deformation of one or more wall of the aperture(s). The aperture(s) associated with the projection(s) and any other slots, opening etc which are provided may be configured to facilitate outward radial expansion of the sheath body by up to around 2 mm (equating to a total increase in cross sectional diameter of the sheath body of up to around 4 mm), or more preferably up to around 1 mm (equating to a total increase in cross sectional diameter of the sheath body of up to around 2 mm).

In a preferred embodiment, the or each projection is capable of being displaced radially outwardly of the sheath body by up to around 6 mm and the sheath body is capable of expanding radially outwardly by up to around 2 mm. Thus, in this preferred embodiment, the overall diameter of the sheath is capable of increasing by up to around 16 mm (12 mm due to the projections and 4 mm due to the sheath body) when the sheath body is fully expanded and diametrically opposite spikes are fully outwardly displaced. In a further preferred embodiment, the or each projection is capable of displacing radially outwardly by up to around 2 mm and the sheath body can expand radially by up to around 1 mm, providing a device in which the cross sectional diameter of the device can increase by up to around 6 mm (4 mm due to the projections and 2 mm due to the sheath body) upon insertion of the member within the inner longitudinal bore of the sheath.

The sheath body of the prototype device used in some of the tests described in the Examples section below was manufactured from relatively inexpensive nylon purely for convenience. The sheath body may in fact be manufactured from any suitable material that is currently employed for graft fixation devices. It is preferred that at least one of said sheath body, projection(s) and member is formed of a surgical grade plastic material. It is particularly preferred that the sheath body and the or each projection are formed from a surgical grade plastic material.

The surgical grade plastic material may be selected from the group consisting of polyetheretherketone, polylactic acid, polyglycolic acid, polycaprolactone, poly(lactic-co-glycolic acid), poly(glycolide-co-caprolactone), poly (glycolide-co-trimethylene carbonate) and mixtures and blends thereof.

At least one of said sheath body, projection(s) and member is preferably formed of a bioabsorbable and/or biodegradable material.

With regard to the member, it is preferred that it is formed of a suitable plastic, or may be formed from any other appropriate material, such as a surgical grade metal, e.g. stainless steel. The member is preferably solid, but may be at least partially hollow. Preferably the member defines a distal end wall and an opposite proximal end wall, said distal and proximal end walls being connected by a side wall. The side wall is preferably tapered radially inwardly from said proximal end wall to said distal end wall, with a preferred taper angle approximately matching the taper angle of the sheath body. It is preferred that the member has a taper angle of up to around 5°, more preferably around 2° to around 5°, yet more preferably around 3° to around 4°, and most preferably around 3.7° to 3.9°. The member preferably possesses a consistent taper along the entire length of its side wall, starting from a diameter of about 9 mm at its proximal end and reducing to about 7 mm at its distal end. The gradient along the member is equivalent to a taper angle of about 3.88° along the member ($\tan^{-1} 2/30$).

The side wall of the member is preferably continuous and most preferably defines a screw thread, which may run continuously over the entire length of the side wall, or just a portion thereof. An inner surface of the sheath body which is arranged to contact the member as the member is inserted is preferably provided with a screw thread which is complementary to the screw thread defined by the side wall of the member. The inner surface of the sheath body may define a screw thread along substantially its full length and/or circumference, or just one or more portions of the inner surface may define a screw thread or roughened surface. It is desirable that the member, when in the form of a screw or partial screw is finished or polished to round-off any sharp edges on the thread profile and produce a smooth, uniform surface finish. At least a portion of the inner surface of the sheath body may define a suitably roughened surface to form an interference fit with the side wall of the member as it is inserted into the longitudinal bore of the sheath.

Additionally or alternatively, the side wall of the member may define a substantially smooth or flat surface. In preferred embodiments of the member in which the side wall of the member tapers from one end to the opposite end, at least a portion of the side wall of the member may extend substantially linearly between said ends so as to define a substantially constant taper along said portion of the side wall of the member, or said portion may curve radially inwardly (to define a concave portion) or radially outwardly (to define a convex portion) between said ends so as to define a varying taper along said portion of the side wall. It will be appreciated that the side wall of the member may define any number of said linear and/or curved portions extending along the length of the member and/or around the circumference of the member. An inner surface of the sheath body, which is arranged to contact the member as the member is inserted, preferably defines a profile which is complementary to the profile of the side wall of the member.

In preferred embodiments, the member has a wedge or peg-like form defining opposite side walls which are linear substantially throughout their length from one end of the member to the opposite end of the member. Where the sheath body is intended to be used with a wedge or peg-like member the inner surface of the sheath body may define a complementary substantially smooth continuous surfaces along substantially its full length, or just one or more portions of the inner surface may define a substantially smooth continuous surface.

The device according to the first aspect of the present invention may comprise a sheath body and member provided with appropriate features to define a ratchet-like mechanism comprising a plurality of teeth on one component which are engaged by a complementary pawl defined by the other component. In a preferred embodiment, the teeth are defined by the internal surface of the sheath body and the member (e.g in the form of a wedge or peg) represents the pawl. In this way, as the member is inserted the sheath body and associated projections are displaced radially outwardly, but the member is then hindered from being withdrawn from the sheath due to engagement of component representing pawl (e.g. the member) by the component representing the teeth (e.g. the sheath body).

In a preferred embodiment of the device of the first aspect of the present invention a diameter of at least one of the proximal end wall of the member and the proximal end wall of the sheath body is about 2 mm to about 6 mm. A longitudinal length of at least one of the sheath body and the member may be about 6 mm to about 18 mm.

It is particularly preferred that a member having a proximal end wall of diameter about 2 mm to about 6 mm has a longitudinal length of about 6 mm to about 18 mm. Moreover, it is preferred that a sheath body having a proximal end wall of diameter about 2 mm to about 6 mm has a longitudinal length of about 6 mm to about 18 mm.

Smaller diameter devices (2-6 mm×6-18 mm) can be used for procedures such as biceps tenodesis, elbow collateral ligament stabilization and medial patello-femoral ligament reconstruction.

In a further preferred embodiment of the device of the first aspect of the present invention a diameter of at least one of the proximal end wall of the member and the proximal end wall of the sheath body is about 6 mm to about 15 mm. A longitudinal length of at least one of the sheath body and the member may be about 20 mm to about 35 mm. It is particularly preferred that a member having a proximal end wall of diameter about 6 mm to about 15 mm has a longitudinal length of about 20 mm to about 35 mm. Moreover, it is preferred that a sheath body having a proximal end wall of diameter about 6 mm to about 15 mm has a longitudinal length of about 20 mm to about 35 mm.

Larger diameter devices (6-15 mm×20-35 mm) can be used for applications where a bulky tendon/synthetic graft is used e.g. Anterior and Posterior Cruciate Ligament Reconstruction and Knee collateral ligament reconstruction/repair.

It may be desirable to produce devices incorporating sheath body in three 'standard' sizes: 6-7 mm diameter×30 mm length, 8-9 mm×30 mm and 10-11 mm×30 mm.

It is preferred that the diameter of the proximal end wall of the member is similar to the external diameter of the proximal end wall of the sheath body. It is more preferred that the diameter of the proximal end wall of the member is substantially the same as the external diameter of the proximal end wall of the sheath body. Preferably a longitudinal length of the sheath body is similar to a longitudinal length of said member. More preferably a longitudinal length of the sheath body is substantially the same as a longitudinal length of the member. In this way, as the member is inserted or screwed into the bore of the sheath body the sheath body is caused to expand or deform, preferably radially outwards, to accommodate the member. As discussed above, expansion or deformation of the sheath body may be facilitated by forming the sheath body from a material having the desired physical characteristics and/or providing appropriate slots, openings, apertures and/or channels in the sheath body.

The proximal and distal end walls of the member may take any convenient form to facilitate insertion of the member into the inner longitudinal bore defined by the sheath body. Preferably, the proximal end wall defines a formation for engagement by a suitable driving tool, such as a screwdriver, to drive the member into the longitudinal bore. By way of example, the proximal end wall may define a slot extending transverse to the longitudinal bore for engagement by a slot-headed screwdriver, a hexagonal depression for engagement by a hex key, or a crossed depression for engagement by a cross-headed screwdriver. The distal end wall of the member may define a substantially flat cross section, or a curved cross section, such that, for example, the member has an outwardly domed or convexly curved distal end wall.

As stated above, the second aspect of the present invention provides use of a device according to the first aspect of the present invention to fix a graft to a support structure, such as, but not limited to, a portion of bone, e.g. a portion of bone within a bone tunnel.

From the foregoing description of the device and methods forming the different aspects of the present invention it will be appreciated that the following advantages are provided: each tendon bundle or strand can be reliably captured or fixed by the device; the graft construct is both stable and rigid; up to 360 degrees graft to bone compression strength can be provided which provides enhanced concentric healing and increased fixation strength. Provision of the device of the present invention in different sizes facilitates maximization of tendon-to-bone contact. No debris is left behind after surgery, the surgical learning curve is short and relatively simple and the inventive device and methods eliminate post-op hardware removal from the surgical site.

The fifth aspect of the present invention provides a method for fixing a graft to a support structure using a device comprising a sheath having a body that defines an inner longitudinal bore and a member for receipt within said bore, said sheath comprising at least one projection that is moveably connected to said sheath body. The method comprises placing the sheath adjacent the graft and the support structure and inserting the member into the bore of the sheath body so as to displace said at least one projection radially outwardly of said sheath body so that said at least one projection contacts the graft and urges it against the support structure.

It will be appreciated that the device forming the first aspect of the present invention is eminently suitable for application in the method forming the fifth aspect of the present invention and that preferred embodiments of the device as set out above may be used in the above defined fifth aspect of the present invention.

With respect to the device to be used in the fifth aspect of the present invention it is preferred that the at least one projection is pivotally or hingedly connected to the sheath body. Preferably the or each projection is biased to at least partially project radially outwardly of the sheath body prior to receipt of said member within said bore. Alternatively, the or each projection may be biased radially inwardly of the sheath body so as not to project radially outwardly of the sheath body prior to receipt of said member within said bore.

Preferably the method further comprises forming a tunnel in the support structure and locating the graft in said tunnel prior to placing the sheath adjacent the graft.

In a further preferred embodiment the method further comprises aligning the projection(s) of the sheath with a region or regions of the graft which are to be fixed to the support structure prior to insertion of the member into the bore of the sheath body.

The support structure may be a bone tunnel, which may be a bone tunnel formed in a tibia.

The method forming the fifth aspect of the presenting invention is preferably used in an anterior cruciate ligament reconstruction procedure to fix an anterior cruciate ligament graft to a wall of a tibial bone tunnel.

A preferred surgical method for implanting a device according to the first aspect of the present invention is as follows. The method set out below describes the fixation of an anterior cruciate ligament graft to a tibial bone tunnel but it will be appreciated that the general approach may be adapted to fix any desirable graft to any form of support structure.

A tibial bone tunnel may be drilled with the use of an appropriate aiming guide. A guide wire may be placed so that it exits at the ACL footprint. An appropriately sized cannulated drill may then be chosen dependent on the graft size, and used to create the tibial tunnel. The use of impaction drills may improve the performance of the fixation. The tibial tunnel may be created initially using a drill, preferably of approximately 7 mm diameter. This may be followed by a larger diameter drill (e.g. an 8.5 mm diameter drill). This is intended to provide a small clearance (e.g. approx. 1.5 mm) between a sheath (e.g. 7 mm diameter sheath) and the tunnel wall. A tapered punch may then be inserted to dilate the tunnel to, for example, 10.5 mm, at the tunnel's entry point and a narrower diameter, for example, 8.5 mm, at the end of the punch. The punch may be marked to allow the punched hole to be substantially the same length as the member to be inserted into the sheath. It is desirable to use the punch so that there is a small clearance of, for example, 1.5 mm between the sheath and tunnel over the length of the sheath. Use of the punch may also advantageously increase the bone density at the bone tunnel wall and thereby the performance of the device of the present invention.

The femoral tunnel may then be created through the tibial tunnel using the appropriately selected off-set guide. Initially a guide wire is placed using the guide and the previously selected cannulated drill used to create the femoral bone tunnel.

A 4 strand looped hamstring graft (or allograft/synthetic graft) may then be pulled into the femoral tunnel through the tibial tunnel and fixed with the Surgeon's choice of recognised methods of fixation.

It is desirable that the graft is tensioned and cycled before fixation. Initially the sheath forming part of the device of the present invention may be inserted using an introducer or insertion tool so that the projections are aligned with the four strands of the graft. The sheath may then be fully inserted before the member is inserted into the sheath at which point the projections are displaced radially outwardly so as to contact and compress the graft strands against the tibial tunnel wall. Fixation of the graft may also be assisted by outward radial expansion of the sheath body upon insertion of the member into the sheath. This expansion is facilitated in part by the apertures defined by the sheath associated with the projections and in part by the flexible properties of the material from which the sheath is manufactured. Typically, the level of outward radial expansion of the sheath body may be up to around 1 mm, which equates to a total increase in cross sectional diameter of the sheath body of up to around 2 mm.

The invention will be further described by way of example only with reference to the following non-limiting Example, Comparative Examples and preferred embodiment of the present invention, with reference to the accompanying figures in which:

FIGS. 1(a)-(c) is a computer simulation illustrating a device according to the first aspect of the present invention at various stages of insertion of the member (shown side on) into the bore of the sheath body (shown in cross section in FIG. 1(a) and side on in FIGS. 1(b) and 1(c));

FIG. 2 is a plot comparing experimental and modelled results for pull-out force (mean value) versus displacement for a bovine flexor tendon graft fixed in a porcine tibia bone using a standard interference screw, which demonstrates the accuracy of the computer model developed to compared the performance of the device of the present invention to the standard interference screw and the Intrafix™ system;

Figure 3A:
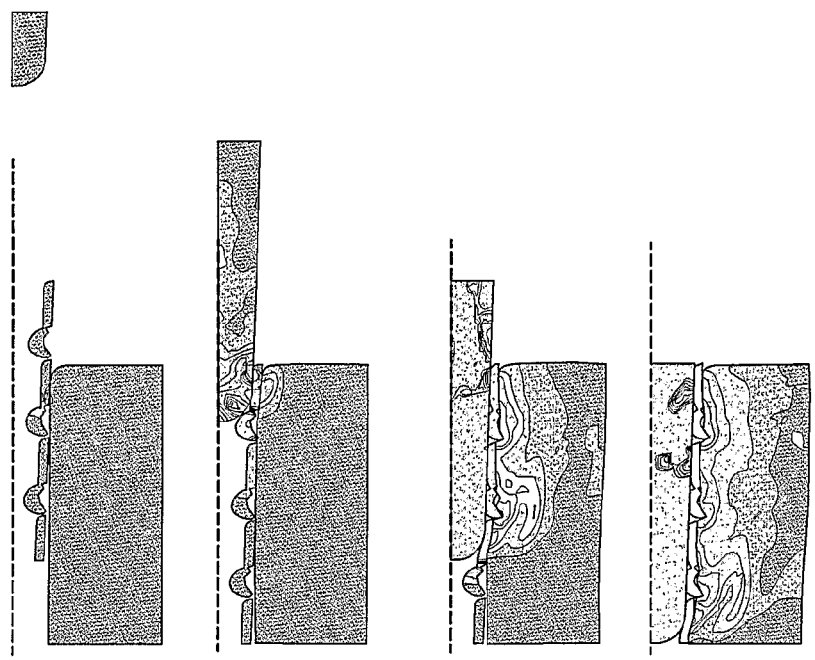
FIG. 3(a) is a computer simulation of stress levels experienced by a device according to a first aspect of the present invention and a bone tunnel wall during a graft fixation as part of an ACL reconstruction procedure. Higher levels of stress on the device and bone tunnel are more lightly coloured and lower levels are more darkly coloured.
Figure 4A:
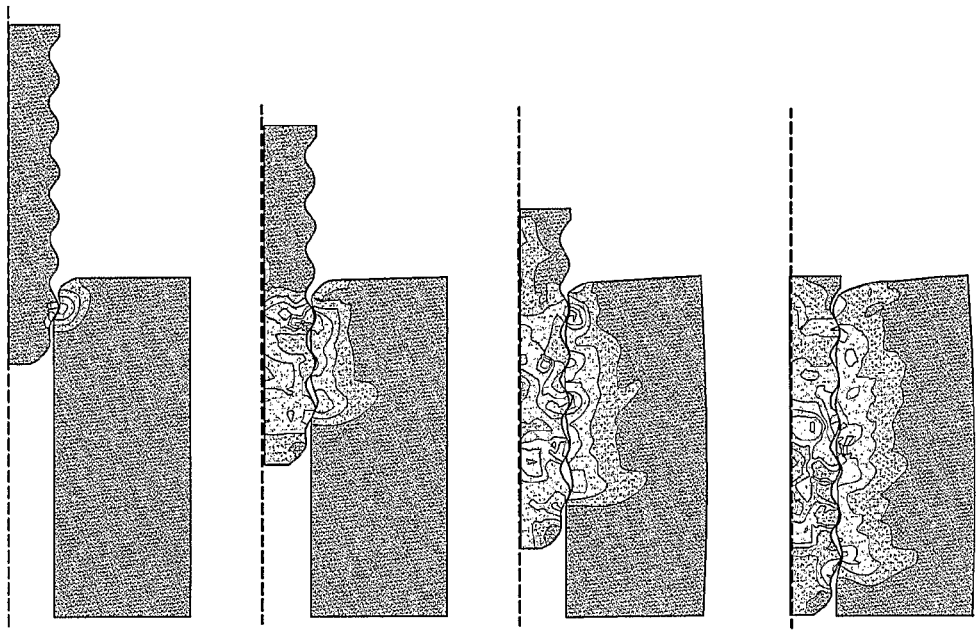
FIG. 4(a) is a computer simulation of stress levels experienced by a conventional fixation screw and a bone tunnel wall during a graft fixation as part of an ACL reconstruction procedure. The same colour coding is used as in FIG. 3(a)
Figure 7:
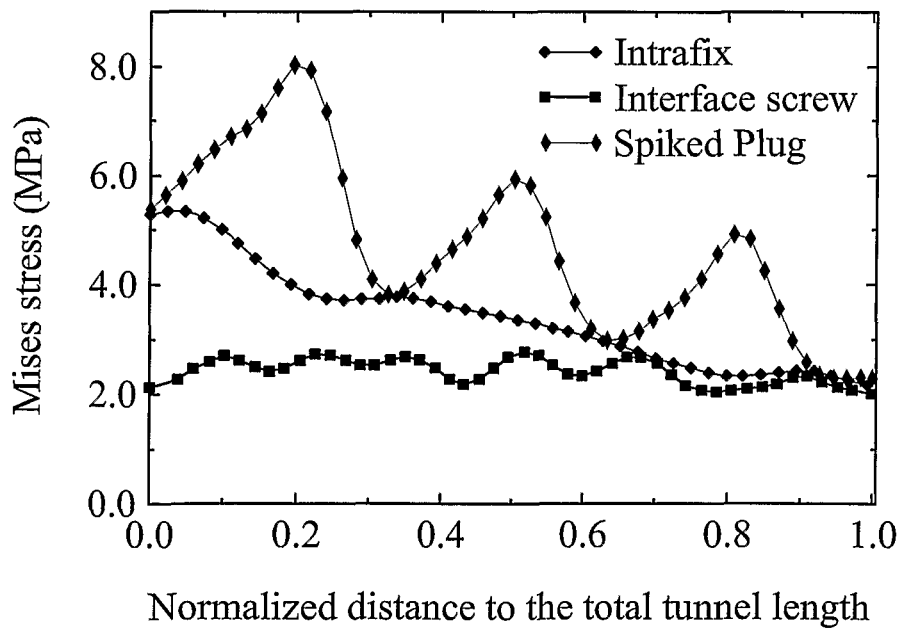
Figure 8:
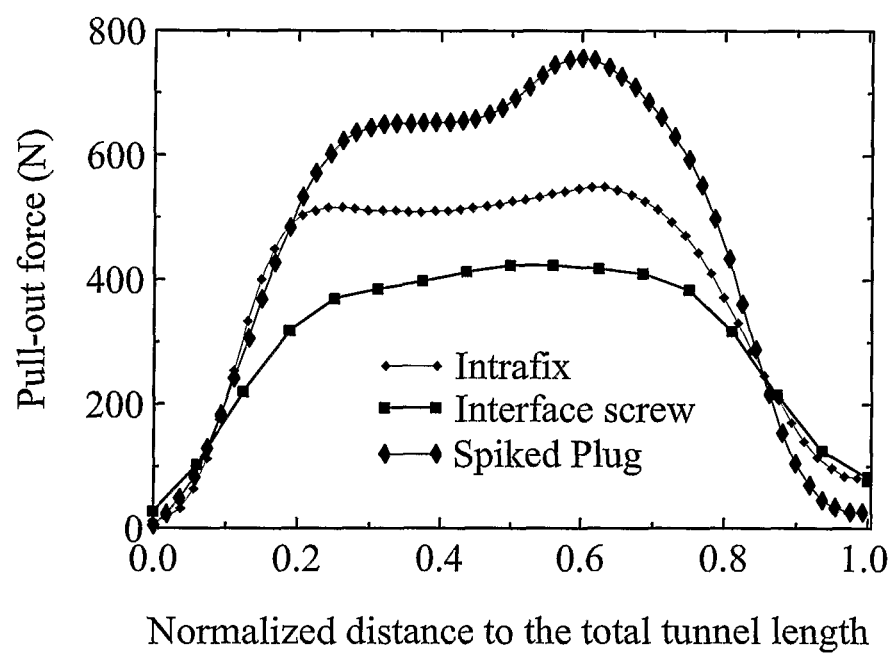

FIG. 7 is a graph comparing tunnel wall stress during fixation for the device of FIG. 3(a) ("Spiked plug"), the screw fastener of FIG. 4(a) ("Interference screw") and the fixation system of FIG. 5(a) ("Intrafix"); and FIG. 8 is a graph prepared using results from the computer modelling which compares the pull-out forces required to remove a tendon graft from a bone tunnel for the inventive device of FIG. 3(a) ("Spiked plug"), the screw fastener of FIG. 4(a) ("Interference screw") and the fixation system of FIG. 5(a) ("Intrafix").

Figure 1A:
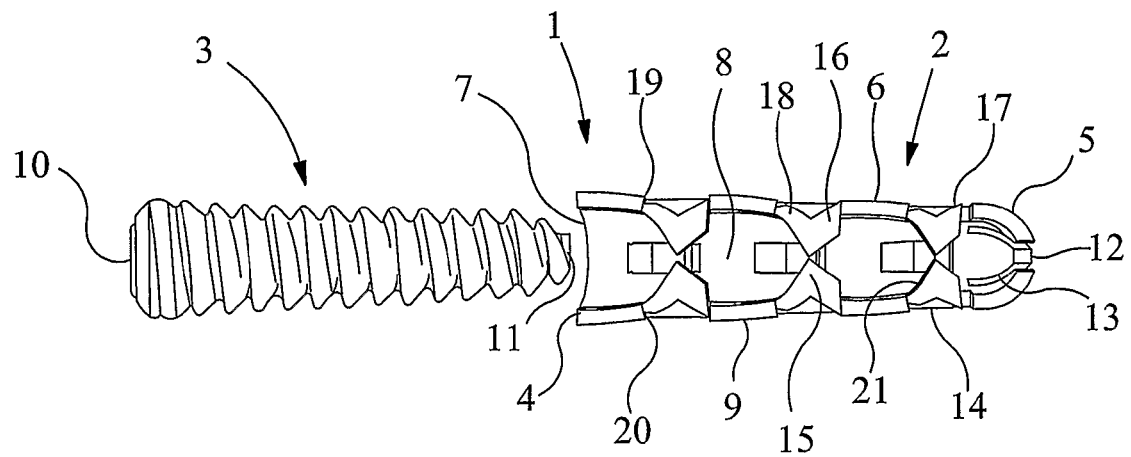
Figure 1B:
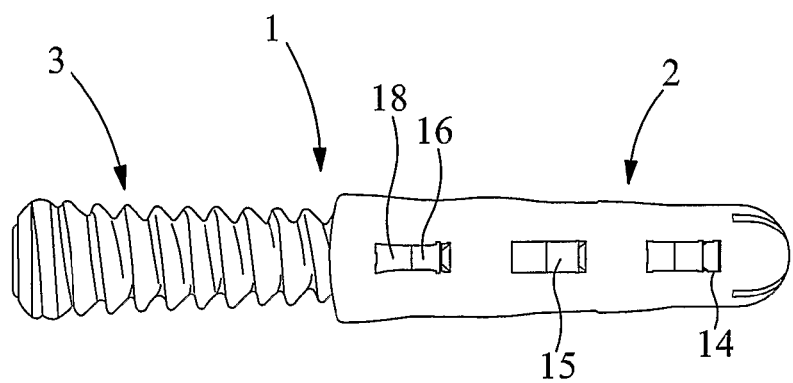
Figure 1C:
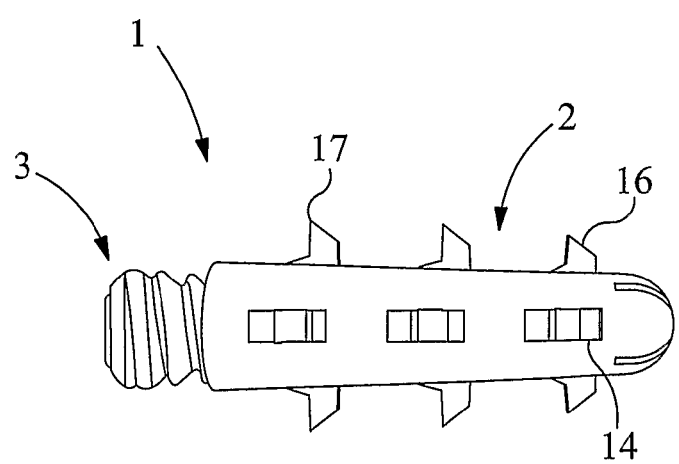

Referring to FIGS. 1(a)-(c) there is shown a graft fixation device 1 comprising a sheath 2 and a screw 3 according to the first aspect of the present invention in various stages of assembly. The sheath 2 is 30 mm long and defines a proximal end wall 4 of 9 mm diameter and a distal end wall 5 of 7 mm maximum diameter separated by a continuous annular side wall 6. The side wall 6 is linearly tapered from the proximal end wall 4 to the distal end wall 5 with a taper angle of 3.88° ($\tan^{-1} 2/30$).

The proximal end wall 4 defines a proximal opening 7 of 7 mm diameter which is of sufficient dimension to facilitate insertion of the screw 3 through the opening 7 into a longitudinal bore 8 defined by the body 9 of the sheath 2.

The screw 3 has the same overall external dimensions as the sheath 2, that is the screw is 30 mm long and tapers linearly from its proximal end 10 (diameter 9 mm) to its distal end 11 (diameter 7 mm). The proximal end 10 of the screw 3 is provided with a slot (not visible in FIGS. 1(a) to 1(c)) for engagement by a suitable driving tool, such as a screwdriver, to drive the screw 3 into the longitudinal bore 8 of the sheath 2. It will be appreciated that the slot could be replaced by any suitable formation, such as a hexagonal depression for engagement by a hex key, or a crossed depression for engagement by a cross-headed screwdriver, to enable the screw 3 to be inserted into the longitudinal bore 8. The distal end 11 of the screw 3 may take any convenient form to facilitate insertion into the sheath 2, in the specific embodiment shown in FIGS. 1(a) to 1(c) the distal end 11 of the screw 3 has a relatively flat cross section, but in further preferred embodiments the screw 3 may have a domed or convexly curved distal end 11.

The distal end wall 5 of the sheath 2 is rounded and defines a central circular distal opening 12 and a plurality of equiangularly spaced longitudinal slots 13.

The side wall 6 of the sheath 2 defines a plurality of rectangular apertures 14 each of which is suitably dimensioned to enable a projection 15 associated with that aperture 14 to move radially in and out of the sheath body 9. The apertures 14 are also configured to deform so as to facilitate outward radial expansion of the sheath body upon insertion of the member 3. The embodiment shown in FIGS. 1(a) to 1(c) incorporates twelve apertures 14 and associated projections 15 arranged in four equiangularly spaced sets of three longitudinally spaced apertures/projections 14/15. Within each set of three apertures/projections 14/15 the apertures 14 are equally longitudinally spaced by 4.5 mm. The aperture 14 closest to the distal end wall 5 of the sheath body 9 is 4.0 mm long and the two remaining apertures 14 are 4.5 mm long. The aperture 14 closest to the distal end wall 5 of the sheath body is longitudinally spaced 2.0 mm from the distal end wall 5, and the aperture 14 closest to the proximal end wall 4 is longitudinally spaced 3.0 mm from the proximal end wall 4.

Each projection 15 comprises a graft engaging portion 16, which terminates with a pointed tip 17, and a connecting portion 18 which connects the graft engaging portion 16 to the body 9 of the sheath 2. The point of connection of each connecting portion 18 to the sheath body 9 defines a living hinge 19 at a proximal edge 20 of the aperture 14. Each connecting portion 18 defines a surface 21 which faces towards the proximal opening 7 and is arranged in this way so that upon insertion of the screw 3 into the bore 8 the screw 3 contacts the surface 21 of each projection 15 and urges that projection 15 radially outwardly of the sheath body 9 through its associated aperture 14. Within each set of three longitudinally spaced projections 15, the surface 21 of the projection 15 closest to the distal end wall 5 of the sheath body 9 is 3.5 mm long and the corresponding surfaces 21 of the two remaining projections 15 are both 4.0 mm long.

When the screw 3 is screwed into the bore 8 of the sheath body 9, as shown in FIGS. 1(b) and 1(c), the screw 3 bears against the surfaces 21 of each group of four equiangularly spaced projections 15 in turn, thereby urging each group of four projections 15 radially outwardly of the sheath body 9 as shown in FIG. 1(c). When the group of four projections 15 closest to the proximal end wall 4 of the sheath body 9 are fully radially extended they provide a maximum cross sectional diameter of 14 mm. When the central group of four projections 15 are full extended they provide a maximum cross sectional diameter of 13 mm, and the projections 15 nearest the distal end wall 5 of the sheath body 9 provide a maximum cross sectional diameter of 12 mm.

An anterior cruciate ligament (ACL) reconstruction employing the device of the present invention begins by drilling a tibial bone tunnel with the use of an appropriate aiming guide. A guide wire is placed so that it exits at the ACL footprint. An appropriately sized cannulated drill is chosen (dependent on the graft size) and is used to create the tibial tunnel. The use of impaction drills improves the performance of the fixation. The tibial tunnel is created initially using a 7 mm diameter drill followed by an 8.5 mm diameter drill. This is intended to provide a 1.5 mm clearance between a sheath having a 7 mm distal diameter and the tunnel wall. A tapered punch is then inserted to dilate the entry point of the tunnel to 10.5 mm leaving the distal end of the tunnel at 8.5 mm diameter. The punch is marked to allow the punched hole to be the same length as the screw which will be inserted into the sheath. It is desirable to use the punch so that there is a small clearance of 1.5 mm between the sheath and tunnel over the length of the sheath.

The femoral tunnel is then created through the tibial tunnel using the appropriately selected off-set guide. Initially a guide wire is placed using the guide and the previously selected cannulated drill used to create the femoral bone tunnel.

A 4 strand looped hamstring graft is then pulled into the femoral tunnel through the tibial tunnel and fixed with the Surgeon's choice of recognised methods of fixation.

The graft should be pre-tensioned, cycled and tensioned before fixation. Initially the sheath is inserted using an introducer so that the projections are aligned with the four strands of the graft. The sheath is then fully inserted before the screw is inserted into the sheath. As the screw is inserted into the sheath the projections are displaced radially outwardly so as to contact and compress the graft strands against the tibial tunnel wall and thereby fix the graft in place.

EXAMPLES

Experimental studies on animal models and computer simulations were carried out in the context of an ACL reconstruction. The experimental tests provided basic material data which was needed to understand the failure modes of ACL reconstruction, as well as to provide information needed for modelling and verification of the simulation. The computer modelling provided technical information which could not have been obtained as easily via pure experimental investigation, such as stress distributions, interfacial loading between the ligament graft, sheath/screw and bones, and first point of failure. The simulation also provided a means to allow various parameters to be tested so as to optimise the design of the fixation device of the present invention without requiring extensive experimental investigation. Experimental tests were then carried out to determine the performance of an unoptimised prototype device according to the present invention for comparison to a commercially available device.

To setup the ACL reconstruction, a tunnel was drilled into a fresh pig or calf tibial bone using a clinical drill bit. A bovine flexor tendon was passed through the tunnel and fixed using standard metal and plastic interference screws. Some of the specimens were sectioned in a frozen state along the axial direction to observe the tibial tunnel structure and interfaces of the fixation into the tibia tunnel. This provided detailed information on the geometric profile for computer modelling. For example, the length and cross-sectional area of the specimens were used for strain and stress calculations. Additionally, non-destructive examination of the ACL reconstruction using x-ray photography was carried out.

Figure 2:
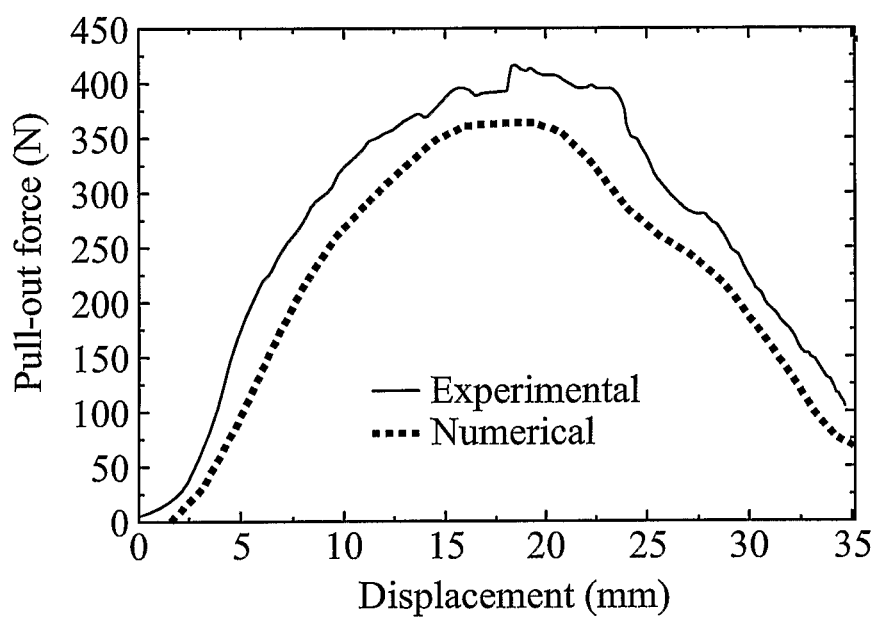

The tendons were tested using screw-driven computer controlled universal tensile test machines. The specimen's response to the loading was obtained in the form of a load-displacement curve. FIG. 2 shows a plot of pull-out force (mean value) versus displacement for a test which used porcine tibial bone and a calf tendon graft. A 10.5 mm tunnel was drilled into the porcine tibial bone. The tendon graft with a total diameter size of 7 mm was inserted into the tunnel with the assistance of sutures hanging from the strands. A loop of tendon approximately 40 mm long was left extending out from the upper part of the tibial bone. The loop was used to hold the graft to a hook in the upper grip of the testing machine.

The sheath forming part of the device of the present invention was placed at the entrance of the bone tunnel and was inserted with the help of a special driver, sliding it between the tendon strands until it was in a position similar to that of the interference screw. The projections (in the form of spikes) connected to the sheath body were retained inside the sheath during insertion. With the sheath inside the bone tunnel, the member (in the form of a tapered screw) was inserted into the inner longitudinal bore of the sheath to expand the sheath in a radial direction and displace the spikes radially outwardly of the sheath body. The tibial bone tail was fixed to the base and the tendon graft was pulled in-line with the axes of the tunnel. The specimen was fixed to the testing machine and the tendon graft then subjected to a standard pull-out test at a rate of 20 mm/min until failure.

In parallel, 3D numerical modelling (explained more fully below) was performed to mimic the experiment. For the sake of the numerical modelling it was assumed that the device did not contact the bone during fixation. The result from the model is also presented in FIG. 2 for comparison.

The agreement between modelled and experimental values was good considering the assumptions made on loading conditions, geometry and material properties and the exclusion of the mechanical influence of the muscles, ligaments and cartilage. The model has provided an insight into the type and magnitude of the forces acting on the bone in ACL reconstruction which has enabled the prediction of patterns of the stress, strain and displacement in the regions around the bone tunnel.

A commercial code, ABAQUS/Explicit, was used to simulate the dynamic turning and advancing of the screw and radial outward displacement of the projections. The bone was modelled using a 3-dimensional solid elements C3D4 element, a 4-node linear tetrahedron provided by the code. This element has the advantage of providing high accuracy in geometric meshing for complicated 3D shapes, which is required for the contact between the bone and the fixation device during the fixation process. Mesh adequacy was validated using a convergence analyses. This was achieved using a standard method whereby the results of several different mesh densities were compared to ensure they were sufficiently close to each other. In this way it was possible to establish an appropriate mesh density which was fine enough, but not so fine as to require extra calculation with effectively no enhancement in the accuracy of the model. The screw was also modelled using the solid elements C3D4 element.

The finite element model was created for a section of tibial bone containing a tunnel and an inserted interference screw, Intrafix™ sheath, and sheath forming part of the device of the present invention. The materials for cortical, cancellous and subchondral bones were assumed linear elastic, which is adequate for most studies of bone stress and strain.[4] The modelled bone was assigned a stiffness value from experimental data. The shear modulus was calculated from empirical relationships reported by Ashman et al.[5] and an isotropic Poisson's ratio was used.[6] Due to scarcity of experimental data, subchondral bone was assumed as isotropic[7,8] and homogeneous.

In the model, a 9 mm diameter tunnel was created at locations reported by Fu et al.[3], i.e. at an angle of about 10° to the midsagittal plane and 45° to the midcoronal plane. The locations were within the boundaries of those used clinically.

The screw or sheath was inserted with a force directed along the tunnel axis (i.e. longitudinally), which has to be equal to the graft tension at full extension of the knee during gait.

The cortical and cancellous bone properties of stiffness and shear modulus were derived from a combination of experimental data obtained during the current study and the open literature.[9,10,11] The stresses in at the interface between the bone and the screw or sheath were examined at different stages of fixation.

Figure 3B:
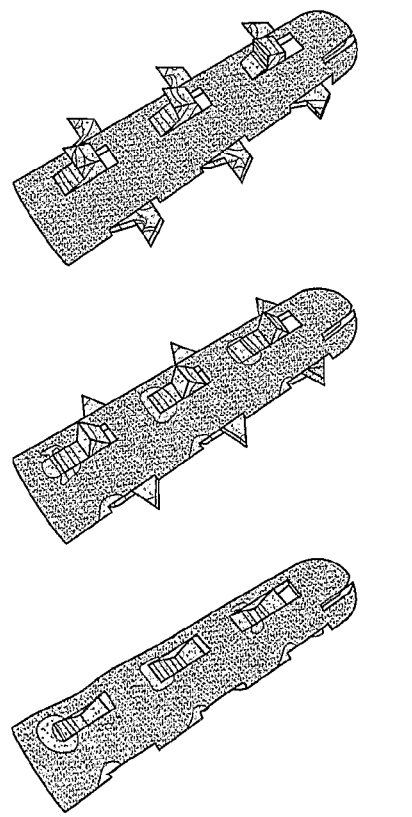
FIG. 3(b) is a finite element model of the device of FIG. 3(a) showing outward radial displacement of projections during insertion of the member into the sheath body. The same colour coding is used as in FIG. 3(a)

FIG. 3(a) is a computer simulation of stress levels experienced by a device according to a first aspect of the present invention and a bone tunnel wall during a graft fixation as part of an ACL reconstruction procedure. Higher levels of stress on the device and bone tunnel are more lightly coloured and lower levels are more darkly coloured. FIG. 3(b) is a finite element model of the device of FIG. 3(a) showing outward radial displacement of projections during insertion of the member into the sheath body.

Experimental tests using a standard testing protocol were conducted to determine the fixation performance of a rudimentary prototype device according to the present invention so that its performance could be compared to a commercially available Intrafix™ device.

The prototype device according to the present invention was manufactured using non-optimised materials (nylon), components (i.e. size and shape of sheath and member) and manufacturing techniques. The prototype device therefore provided only an initial indication of the potential capabilities of the device. Testing was carried out using six samples of the prototype device and six samples of the Intrafix™ device using porcine tibial bone and bovine flexor tendon graft.

COMPARATIVE EXAMPLES

Computer simulations of two different prior art methods of screw fixation have been carried out. Several models have been developed which facilitated the simulations of the installation of the screw, the deformation of the ligament, as well as the distribution of the stress in both the bone and the ligament to be analysed. Using actual experimental data allowed the input of the modelling to be updated so as to allow for more accurate simulation of the mechanical environment. Comparative tests were then carried out to compare the performance of an unoptimised prototype device according to the present invention to a commercially available device.

Comparative Example 1

Figure 4B:
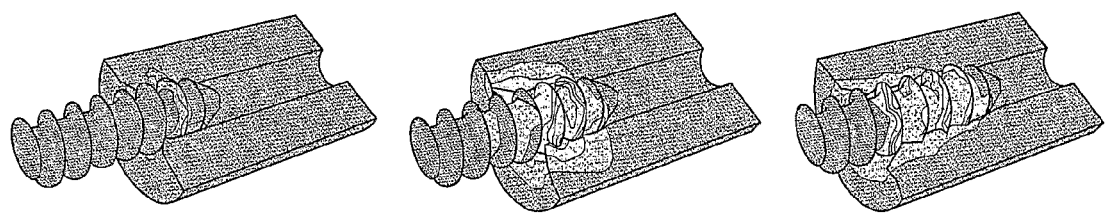
FIG. 4(b) is a computer simulation of stress levels experienced by a conventional fixation screw at discrete stages of insertion of the screw into a tibial bone tunnel (shown in cross section) as a part of an ACL reconstruction procedure. The same colour coding is used as in FIG. 3(a)
Figure 4C:
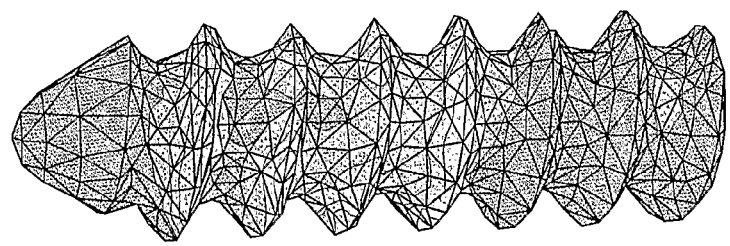
FIG. 4(c) is a finite element model of the screw of FIGS. 4(a) and 4(b) illustrating stress levels experienced during insertion of the screw as a part of an ACL reconstruction procedure. The same colour coding is used as in FIG. 3(a)

FIG. 4(a) is a computer simulation of stress levels experienced by a conventional fixation screw and a bone tunnel wall during a graft fixation as part of an ACL reconstruction procedure. The same colour coding is used as in FIG. 3(a). FIG. 4(b) is a computer simulation of the stages of insertion of a conventional fixation screw into a tibial tunnel during an ACL reconstruction. FIG. 4(c) is a finite element model of the screw of FIGS. 4(a) and 4(b) illustrating stress levels experienced during insertion of the screw as a part of an ACL reconstruction procedure.

Comparative Example 2

Intrafix™ from DePuy Mitek (a Johnson & Johnson company) is a soft tissue tibial fixation system for anterior cruciate ligament reconstruction. The Intrafix™ system has been in clinical use since 1999. The Intrafix™ (non-absorbable) and bio-Intrafix™ soft tissue fasteners are patented tibial fixation systems, designed to maximize the strength and stiffness of an ACL reconstruction using soft tissue grafts.

Figure 5:
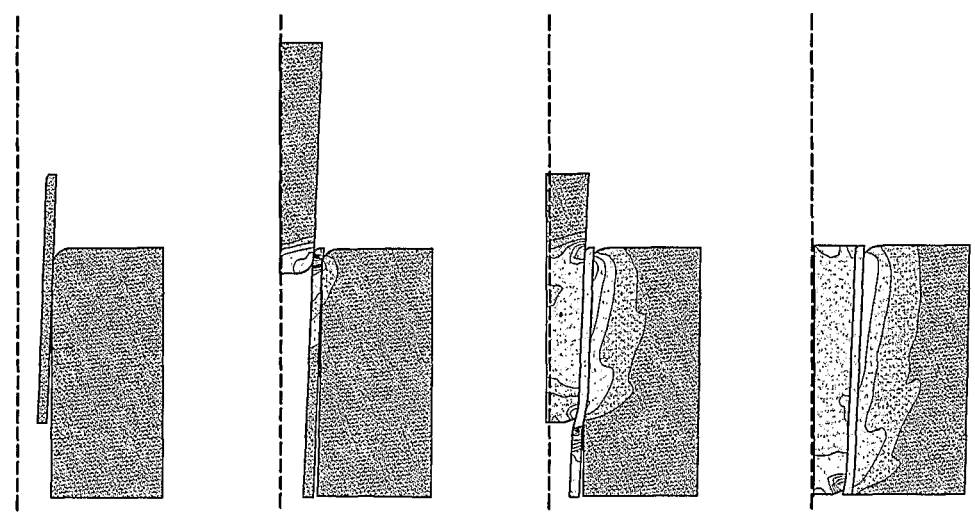
FIG. 5 is a computer simulation of stress levels experienced by a prior art fixation system (Intrafix™) which employs a sheath and an expansion member, and a bone tunnel wall during a graft fixation as part of an ACL reconstruction procedure. The same colour coding is used as in FIG. 3(a)

FIG. 5 is a computer simulation of stress levels experienced by an Intrafix™ fixation system and a bone tunnel wall during graft fixation as part of an ACL reconstruction procedure. The same colour coding is used as in FIG. 3(a).

Comparative Example 3

A further computer model was developed to compare the fixation strength of the interference screw, Intrafix and device of the present invention. The same boundary condition and failure mode were assumed for all three types of device. Therefore, the results provide useful comparative values rather than providing actual numerical data for the devices which could be compared to experiment. For this reason a 2D axisymmetric finite element explicit method was used in this analysis.

For all three types of device an 8 mm cylindrical tunnel was created. The diameter of the tunnel was chosen to be smaller than the maximum diameter of the fixation device to cover the differences between the shapes of the devices.

The same material property was assumed for the tibial bone tunnels (based on the human bone). For the device of the present invention, stainless steel and Nylon were defined for the member and sheath respectively. The materials were modelled as exhibiting uniform linear elastic behaviour. No viscosity or yield/failure was defined for the materials in these tests.

The external boundary of the tunnel was restricted in the axial direction and the boundary assumed non-reflective.

An interaction (penalty contact method) was defined between the bone and device. The friction coefficient between the screw to bone; sheath to bone; and member to sheath was assumed as 0.35, 0.3 and 0.25 respectively. A linear displacement boundary equal to the tunnel length was defined for the screw, pin and sheath to fully place inside the tunnel. No rotational motion was assumed for the screw, pin or sheath during insertion.

The interference screw was modelled with a rounded pitch (no sharp edges) but the tapered screw in the Intrafix™ and the member used with the inventive device was assumed as a smooth pin to simplify the analysis.

Comparative Example 4

Cyclic-loading testing evaluates the cyclic behaviour of a graft-fixation construct, and thus, better allows the determination of immediate post-operative changes which may occur.

In order to compare the dynamic strength of an interference screw fixation method with a device of the present invention, several porcine tibial bones with bovine flexor tendon graft were cyclically tested.

Figure 6:
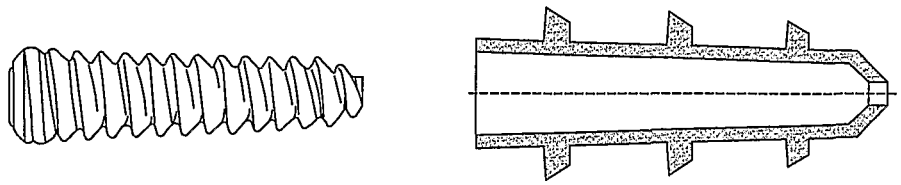
FIG. 6 are schematic drawings of a member and sheath according to the present invention showing the dimensions of various features in mm.

Tendon grafts were fixed into bone tunnels with 35 mm long metal interference screws or devices according to the present invention (dimensions as shown in FIG. 6). A preload of 5 N was used before repetitive loading in the direction parallel to the long axis of the bone tunnel. The specimens were loaded cyclically with the loading axis in line with the graft-bone tunnel at a frequency of 1.0 Hz. The graft was then cycled in two stages as follows.

First, each graft was loaded in tension from 50 N to 150 N (100±50N) at the different number of cycles. After loading in each cycle, the graft was unloaded and allowed to rest for 5 seconds before reloading. This was followed by measurement of the graft displacement. In a 1000 cycle loading test, the construct was unloaded in 1 second and left under zero load for 60 seconds before reloading, to allow time-dependent recovery of the graft.

Second, each graft was loaded at 200 to 400 N (300±100N) with a different number of cycles followed with a 5 second rest and measuring the graft displacement.

After conducting each cyclic loading test, the graft was subjected to a load to failure under a constant rate of displacement parallel to the axis of the grafts if the fixation had survived.

The results of these tests are presented below in Table 2.

Comparative Results

FIG. 7 is a graph of the results generated in Comparative Example 3 above, which compares tunnel wall stress during fixation for the device of the present invention ("Spiked plug") to the conventional screw fastener from Comparative Example 1 ("Interference screw") and the Intrafix™ fixation system of Comparative Example 2. The minimum level of stress on the tunnel wall was provided by the conventional screw and the maximum level of stress was provided by the device of the present invention, which indicates that the device of the present invention forced the graft ligament against the bony tunnel with the greatest force of the three fixation methods under comparison.

FIG. 8 is a graph comparing the pull-out forces required to remove the graft from a bone tunnel for the device of the present invention ("Spiked plug"), the standard interference screw fastener from Comparative Example 1 and the Intrafix™ fixation system of Comparative Example 2. The maximum pull-out force exhibited by any of the three fixation systems under comparison was just over 700 N, which was exhibited by the device of the present invention (see Table 1). This level of force is up to 180% higher than the standard interference screw and up to 130% higher than the level exhibited by the Intrafix™ system. The maximum pull-out force exhibited by the device of the present invention is also significantly greater than the threshold pull out force of 500 N, which ACL surgeons recommend.

TABLE 1

| Fixation System | Maximum pull-out force | Percentage |
|---|---|---|
| Screw | 422.7 N | 100% |
| Intrafix ™ | 578.6 N | 129.8% |
| Inventive Device | 757.7 N | 179.3% |

The results of the cyclic loading tests are presented below in Table 2. In conclusion, all grafts employing the conventional screw fixation method failed at the fixation site with the tendon being pulled past the screw when the initial loading of the second round cyclic loading was applied. In contrast, when the device of the present invention was used the specimen survived the cyclic loading and so a load to failure could be applied. The load at failure was over 500 N for all of the tests carried out using devices according to the present invention. It was also observed during the cyclic loading tests that the applied force at initial slippage for each of the graft strands was significantly higher when using the device of the present invention compared to the conventional interference screw.

TABLE 2

| Number of cycles | Graft elongation (mm) | |
|---|---|---|
| | Interference Screw | Inventive Device |
| 150N (100 ± 50N) Loading at 1 Hz | | |
| 10 | 0.90 | 0.53 |
| 50 | 1.71 | 0.87 |
| 100 | 1.80 | 1.27 |
| 200 | 2.08 | 1.52 |
| 300 | 2.21 | 1.80 |
| 400 | 2.26 | 1.92 |
| 500 | 2.42 | 1.97 |
| 750 | 2.68 | 2.29 |
| 1000 | 2.82 | 2.44 |
| 400N (300 ± 100N) loading at 1 Hz | | |
| 10 | 6.81 fixation failed | 3.47 |
| 50 | — | 3.89 |
| 100 | — | 4.43 |
| 200 | — | 4.74 |
| 300 | — | 4.91 |
| 400 | — | 5.19 |
| 500 | — | 5.35 |
| 750 | — | 5.68 |
| 1000 | — | 5.88 |

The results presented below in Table 3 compare the performance of the prototype device according to the present invention to a commercially available Intrafix™ device in standard tests conducted to determine the ability of the devices to fix a bovine flexor tendon graft to porcine tibial bone.

It can be observed from the results that even a rudimentary unoptimised prototype device according to the present invention performs approximately as well as the commercially available product (i.e. there was no statistically significant difference in the performance of the two types of devices), suggesting that with further development, the device according to the present invention is likely to outperform current commercially available devices, such as the Intrafix™ device.

TABLE 3

| Sample | Yield Point (N) | Ultimate load to failure (N) | Stiffness (N/mm) | *Cyclical Displacement (mm) | Load required for 5 mm tendon displacement (N) | Mode of Failure |
|---|---|---|---|---|---|---|
| Inventive Device | | | | | | |
| 1 | 992 | 992 | 379 | 1.69 | 911 | tendon slipped past fixation |
| 2 | 935 | 935 | 286 | 2.36 | 768 | tendon slipped past fixation |
| 3 | 1227 | 1227 | 263 | 2.79 | 718 | tendon slipped past fixation |
| 4 | 1032 | 1032 | 245 | 2.30 | 753 | tendon slipped past fixation |
| 5 | 1553 | 1553 | 235 | 2.57 | 736 | tendon slipped past fixation |
| 6 | 1181 | 1217 | 235 | 2.89 | 700 | tendon slipped past fixation |
| Average | 1153 | 1159 | 274 | 2.43 | 764 | |
| St. Dev. | 226 | 227 | 55 | 0.43 | 76 | |
| IntraFix ™ Device | | | | | | |
| Average | 1271 | 1376 | 256 | 2.73 | 791 | |
| St. Dev. | 317 | 407 | 58 | 0.29 | 156 | |

(*displacement for the tendon after 500 cycles from 0 to 400 N applied load)

References

1. C. B. Frank and D. W. Jackson, 1997. Current Concepts Review—The Science of Reconstruction of the Anterior Cruciate Ligament, J. Bone Joint Surg. Am. 79, 1556-76.
2. C. D. Harner, et al., Evaluation and Treatment of Recurrent Instability After Anterior Cruciate Ligament Reconstruction. Selected Instructional Course Lectures, The American Academy Of Orthopaedic Surgeons.
3. F. H. Fu, C. H. Bennett, C. B. Ma, J. menetrey, C. Lattermann, 2000. Current trends in anterior cruciate ligament reconstruction. Part II: Operative procedures and clinical correlations. American Journal of Sports Medicine 28, 124-130.
4. S. C. (Ed.) Cowin, 1989. Bone Mechanics. CRC Press, Boca Raton, Fla.
5. R. B. Ashman, J. Y. Rho, C. H. Turner, 1989. Anatomical variation of orthotropic elastic moduli of the proximal human tibia. Journal of Biomechanics 22, 895-900.
6. J. L. Williams, J. L. Lewis, 1982. Properties and an anisotropic model of cancellous bone from the proximal tibial epiphysis. Transactions of ASME, Journal of Biomechanical Engineering 104, 50-56.
7. K. Choi, J. L. Kuhn, M. J. Ciarelli, S. A. Goldstein, 1990. The elastic moduli of human subchondral, trabecular, and cortical bone tissue and the size-dependency of cortical bone modulus. Journal of Biomechanics 23, 1103-1113.
8. T. D. Brown, A. M. DiGioia, 1984. A contact-coupled finite element analysis of the natural adult hip. Journal of Biomechanics 17, 437-448.
9. J. Y. Rho, 1992. Mechanical properties of cortical and cancellous bone. Ph.D. Dissertation, University of Texas Southwestern Medical Center, Dallas, Tex., USA.
10. R. B. Bourne, J. B. Finlay, P. Papadopoulos, C. H. Rorabeck, P. Andreae, 1984. In vitro strain distribution in the proximal tibia. Clinical Orthopaedics and Related Research 188, 285-291.
11. D. Reilly, P. S. Walker, M. Ben-Dov, F. C. Ewald, 1982. Effects of tibial components on load transfer in the upper tibia. Clinical Orthopaedics and Related Research 165, 273-282.

The invention claimed is:

1. A graft fixation device comprising:
a sheath having a sheath body that defines an inner longitudinal bore, wherein the sheath body includes a proximal end, a distal end and a side wall; and
a member for receipt within said bore, said member being a tapered threaded screw,
wherein said sheath body comprises a plurality of longitudinally spaced projections movably connected to said sheath body and a plurality of apertures associated with the plurality of longitudinally spaced projections to allow the plurality of longitudinally spaced projections to move radially out of the sheath body and through an associated aperture, and wherein said projections are hinged on one side so as to be displaceable radially outwardly relative to said sheath body and through the associated aperture upon receipt of said member within said bore, wherein each of the plurality of longitudinally spaced projections comprises a graft engaging portion terminating in a pointed tip and a connecting portion connecting the graft engaging portion to the sheath body, each connecting portion defining a surface which faces towards the proximal end of the sheath body and is arranged so that, upon insertion of the threaded screw into the longitudinal bore, the threaded screw contacts the surface of each connecting portion of the plurality of longitudinally spaced projections, and
wherein said side wall is tapered radially inwardly from said proximal end to said distal end, and said distal end has a rounded distal end wall to allow sliding of the graft fixation device between graft strands when the graft fixation device is inserted into a bone tunnel, the rounded distal end wall defining a central circular distal opening and a plurality of equiangularly spaced longitudinal slots.

2. A device according to claim 1, wherein each projection is outwardly radially displaceable through the aperture, wherein the aperture is provided in the side wall of the sheath body.

3. A device according to claim 1, wherein each projection is biased to project radially outwardly of the sheath body prior to receipt of said member within said bore.

4. A device according to claims 1, wherein each projection is biased radially inwardly of the sheath body so as not to project radially outwardly of the sheath body prior to receipt of said member within said bore.

5. A device according to claim 1, wherein each projection includes a connecting portion and a graft engaging portion, the connecting portion of the projection comprising a surface facing towards said proximal opening of the sheath body, said surface being arranged so as to be contactable by said member upon insertion of the member into said bore.

6. A device according to claim 5, wherein said graft engaging portion and said connecting portion of each projection are integrally formed.

7. A device according to claim 1, wherein the device comprises three projections provided at positions that are equally longitudinally spaced along said sheath body.

8. A device according to claim 1, wherein said sheath body is deformable radially outwardly upon receipt of said member within said bore.

9. A device according to claim 1, wherein said side wall defines a screw thread and/or a substantially flat surface.

10. A device according to claim 1, wherein at least one of said sheath body, projection(s) and member is formed of a surgical grade plastic.

11. A device according to claim 1, wherein at least one of said sheath body, projection(s) and member is formed of a bioabsorbable or biodegradable material.

12. A device according to claim 1, wherein the longitudinal length of said sheath body is similar to a longitudinal length of said member.

* * * * *